United States Patent
Celmins et al.

(10) Patent No.: US 10,984,916 B2
(45) Date of Patent: *Apr. 20, 2021

(54) MODULAR TELEHEALTH CART WITH THERMAL IMAGING AND TOUCH SCREEN USER INTERFACE

(71) Applicant: INTOUCH TECHNOLOGIES, INC., Goleta, CA (US)

(72) Inventors: John Celmins, Santa Barbara, CA (US); Gary Douville, Santa Barbara, CA (US); Daniel Sanchez, Goleta, CA (US); Marco Pinter, Santa Barbara, CA (US); Charles S. Jordan, Santa Barbara, CA (US); Yulun Wang, Goleta, CA (US)

(73) Assignee: TELADOC HEALTH, INC., Purchase, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/687,431

(22) Filed: Nov. 18, 2019

(65) Prior Publication Data
US 2020/0265961 A1 Aug. 20, 2020

Related U.S. Application Data

(63) Continuation of application No. 16/045,600, filed on Jul. 25, 2018, now Pat. No. 10,483,007.
(Continued)

(51) Int. Cl.
*G16H 80/00* (2018.01)
*H04N 5/247* (2006.01)
(Continued)

(52) U.S. Cl.
CPC .......... *G16H 80/00* (2018.01); *G06F 1/1613* (2013.01); *G06F 1/1632* (2013.01); *G16H 40/63* (2018.01); *G16H 40/67* (2018.01); *H04N 5/2251* (2013.01); *H04N 5/2257* (2013.01); *H04N 5/2258* (2013.01); *H04N 5/23206* (2013.01); *H04N 5/23216* (2013.01); *H04N 5/23296* (2013.01); *H04N 5/23299* (2018.08);
(Continued)

(58) Field of Classification Search
CPC .......... G16H 80/00; G16H 40/67; H04N 5/44; H04N 5/247; H04N 5/225; H04N 5/232; H04N 7/14; H04N 7/15
USPC ............................. 348/14.01–14.16; 434/262
See application file for complete search history.

(56) References Cited

U.S. PATENT DOCUMENTS

| | | | | |
|---|---|---|---|---|
| 2001/0048464 A1* | 12/2001 | Barnett | .................. | H04N 7/142 348/14.08 |
| 2006/0271409 A1* | 11/2006 | Rosenfeld | .............. | G06Q 50/22 705/3 |

(Continued)

OTHER PUBLICATIONS

Avizia CA750 User & Installation Guide, 2017, avizia.com.

*Primary Examiner* — Melur Ramakrishnaiah

(57) ABSTRACT

A telemedicine system including a cart that allows for two-way audio/video conferencing between patients or local care providers and remote care providers or family members. The cart employs a modular design that allows its capabilities to be expanded to meet the needs of particular telemedicine applications. In addition, the cart provides thermal imaging and a user interface that allows local care provers to access various capabilities of the device while the device is not in session with a remote party.

20 Claims, 9 Drawing Sheets

Related U.S. Application Data

(60) Provisional application No. 62/536,907, filed on Jul. 25, 2017.

(51) Int. Cl.
| | |
|---|---|
| *H04N 5/225* | (2006.01) |
| *H04N 5/232* | (2006.01) |
| *H04N 7/14* | (2006.01) |
| *H04N 7/15* | (2006.01) |
| *G06F 1/16* | (2006.01) |
| *G16H 40/67* | (2018.01) |
| *G16H 40/63* | (2018.01) |
| *H04N 21/422* | (2011.01) |
| *G06F 3/0482* | (2013.01) |

(52) U.S. Cl.
CPC ....... *H04N 5/232061* (2018.08); *H04N 5/247* (2013.01); *H04N 7/142* (2013.01); *H04N 7/147* (2013.01); *H04N 7/15* (2013.01); *H04N 21/42204* (2013.01); *G06F 3/0482* (2013.01); *H04N 21/42208* (2013.01); *H04N 21/42224* (2013.01)

(56) References Cited

U.S. PATENT DOCUMENTS

| | | | |
|---|---|---|---|
| 2015/0081338 A1* | 3/2015 | Lai | B25J 9/1676 705/3 |
| 2016/0042139 A1* | 2/2016 | Uttley | B62B 1/26 280/652 |
| 2016/0328532 A1* | 11/2016 | Rieder | F16M 11/28 |
| 2018/0008360 A1* | 1/2018 | Costa da Cruz | G06F 19/3418 |

* cited by examiner

MODULAR TELEHEALTH CART WITH THERMAL IMAGING AND TOUCH SCREEN USER INTERFACE

CROSS-REFERENCE TO RELATED APPLICATIONS

This application is a continuation of U.S. application Ser. No. 16/045,600, filed Jul. 25, 2018, pending, which claims priority to U.S. Application No. 62/536,907, filed Jul. 25, 2017, the contents of which are hereby incorporated by reference.

BACKGROUND

Telemedicine, also referred to as telehealth, generally refers to the use of technology to enable physicians or other healthcare providers to examine and treat or recommend treatment for a remotely located patient. Although telemedicine can be practiced using technology as simple as a telephone, the telemedicine solution market today includes devices and software having a wide range of sophistication. Examples of telemedicine devices include the INTOUCH XPRESS, INTOUCH VICI, INTOUCH VANTAGE, INTOUCH LITE, and INTOUCH VITA, all marketed by INTOUCH TECHNOLOGIES, INC., of Goleta, Calif.

The range of solutions generally intends to satisfy the functional and economic requirements of telemedicine encounters in different types of settings with varying levels of acuity. For example, smartphones, tablets, or laptop computers with basic audiovisual capabilities may be sufficient for a patient to consult with their doctor on treating a cold or behavioral health issues. These types of devices, however, may be insufficient in a higher acuity setting such as a hospital emergency department, intensive care unit, or specialty clinic, where the remote physician may require more capable video or imaging devices and/or the ability to monitor data from peripheral medical devices in real time. Other settings where telemedicine is practiced may present other unique requirements.

Thus, the telemedicine solution market is replete with disparate devices and software solutions that seek to satisfy the varied requirements of many different telehealth encounter settings. In addition, while many of these devices offer great value in terms of their ability to provide real-time audio/video consultation between remote parties, few of these devices provide any value to local care providers when not being used in a session with a remote care provider.

SUMMARY

It would be desirable to provide a telemedicine device with broader economic suitability by employing a modular design that allows the device's functionality to be expanded for applications that demand it. For example, it would be beneficial to include an integrated overhead boom camera for neonatal intensive care applications or any application involving a sterile field. Further, it would be beneficial to include an integrated peripheral expansion bay and/or thermal camera for certain care applications.

In addition, it would be desirable to provide a telemedicine device that includes features and/or services that can be utilized by local care providers even when a remote care provider is not logged in to the device. For example, it would be valuable to allow local care providers to request a remote consultation from the device itself. The request for consultation could be for a medical consultation with a remote physician, a family member consultation with a member of the patient's family, or a language translation service in situations where the patient and/or members of the care team do not speak a common language. It would also be valuable to allow local care providers to control any cameras installed on the device and monitor video from these cameras on a display of the telemedicine device when the device is not in session with a remote care provider.

To achieve these ends, one aspect of the disclosure includes a telemedicine system comprising a cart that supports a controller coupled to a camera system, a touchscreen display, a microphone, a speaker, and a network. The controller is configured to display a user interface on the touchscreen display in response to a user input received via the touchscreen display. The user interface includes at least a first selectable option that causes video captured by the camera system to be displayed on the touchscreen display and a second option to transmit a request for consultation via the network. The telemedicine system also includes a remote device coupled to the controller via the network. The remote device includes a camera, a display, a microphone, and a speaker. The remote device is configured to establish a communication session with the controller. During the communication session, the controller causes the touchscreen display to display video captured by the camera of the remote device.

DETAILED DESCRIPTION

The following disclosure includes a telemedicine system including a cart that allows for two-way audio/video conferencing between patients or local care providers and remote care providers or family members. The cart employs a modular design that allows its capabilities to be expanded to meet the needs of particular telemedicine applications. In addition, the cart provides a number of features to local care provers that can be accessed while the device is not in session with a remote party.

Figure 1:
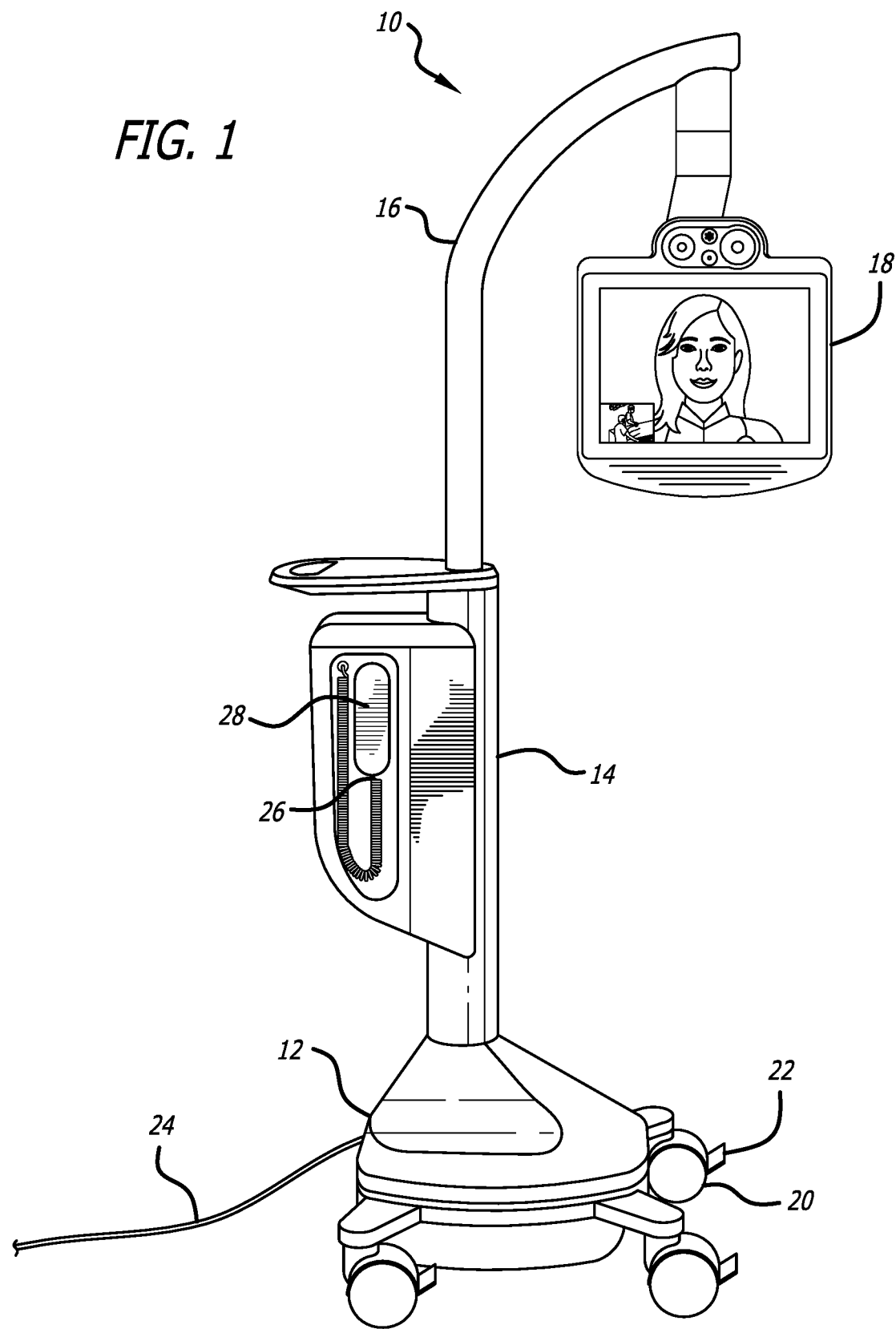
FIG. 1 illustrates a view of a telemedicine cart in accordance with the disclosure.
Figure 2:
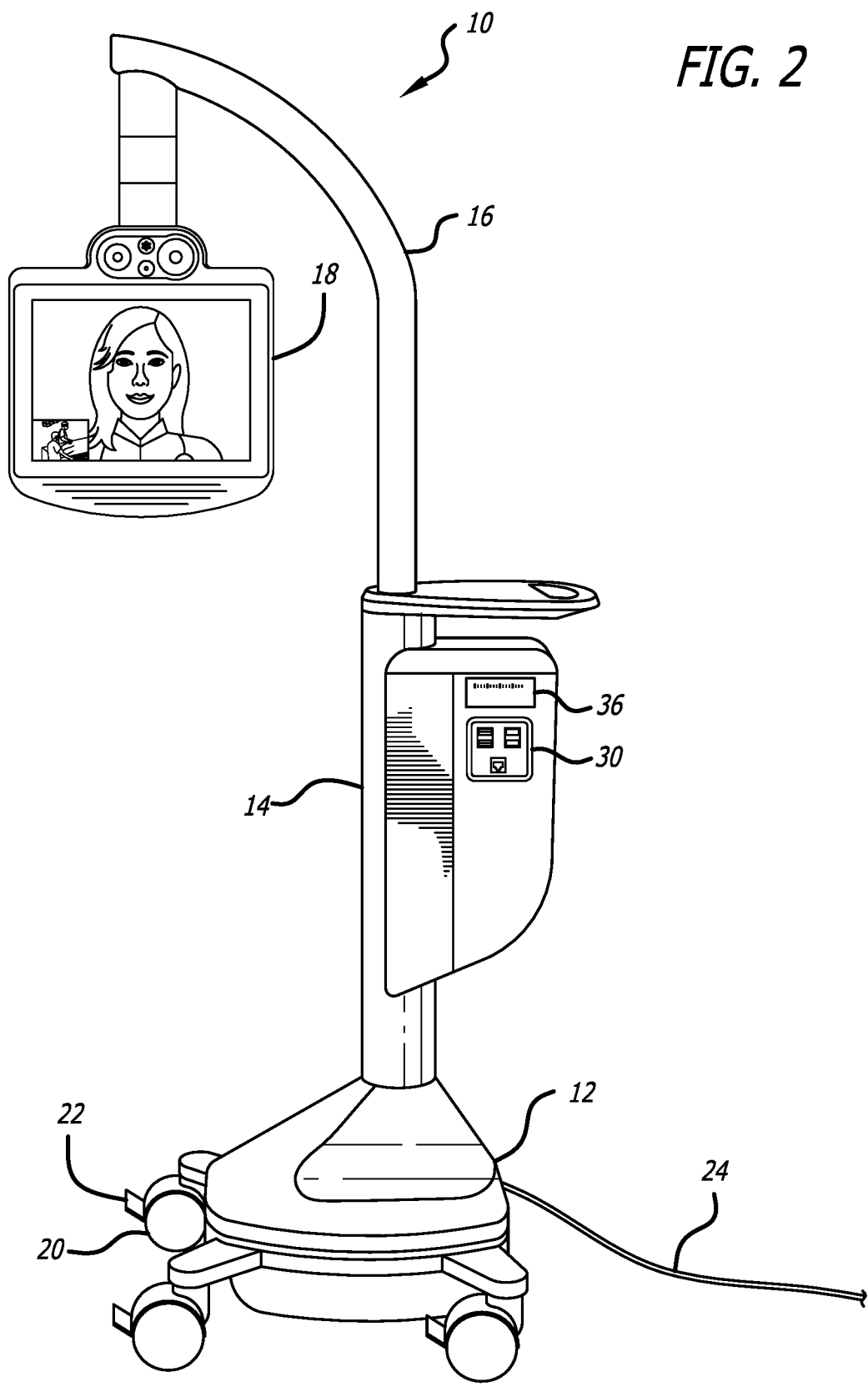
FIG. 2 illustrates a second view of a telemedicine cart in accordance with the disclosure.

FIGS. 1-2 illustrate several views of an example of a telemedicine cart 10 in accordance with the disclosure. The cart 10 includes a base 12, a trunk 14, a neck 16, and a head 18. The base 12 may include casters 20 that allow the cart 10 to be wheeled around a healthcare facility. The casters 20 may include wheel locks 22 for locking the wheels and immobilizing the cart 10 in its desired location. The base 12 may house one or more batteries (not shown) that power the various electrical and electronic components of the cart. The base may also house a battery charger coupled to a power supply that includes an AC power cord 24 that can be plugged into a wall socket to energize the power supply.

Figure 3:
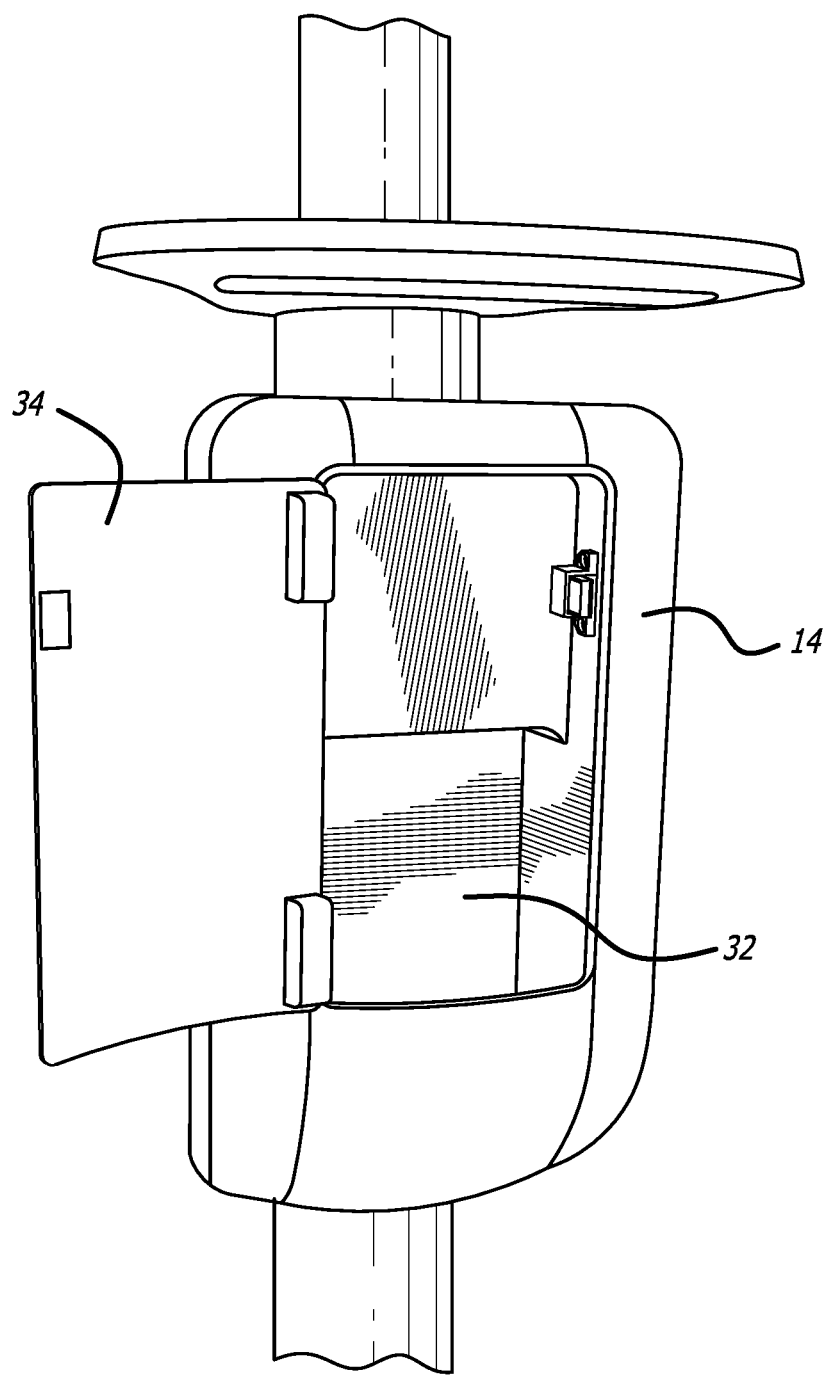
FIG. 3 illustrates a rear view of a telemedicine cart in accordance with the disclosure.

The trunk may include a receptacle 26 for a privacy handset 28 that allows a person in the vicinity of the cart 10 to communicate privately with a remote user logged into the device. As shown in FIG. 2, the trunk 14 may also include a peripheral expansion bay 30 that includes one or more communication ports, including USB ports, HDMI ports, ETHERNET ports, etc. The trunk 14 may also include a status indicator panel 36 that displays the status of various elements of the cart. For example, the status indicator panel 36 may display current battery life or charge level and wireless network strength. As shown in FIG. 3, the rear of the trunk may also include a storage bin 32 with a door 34 that can be shut and latched. The storage bin 32 may be used to stow medical peripherals when not use. Examples of medical peripherals include stethoscopes, otoscopes, dermal cameras, etc.

Figure 4:
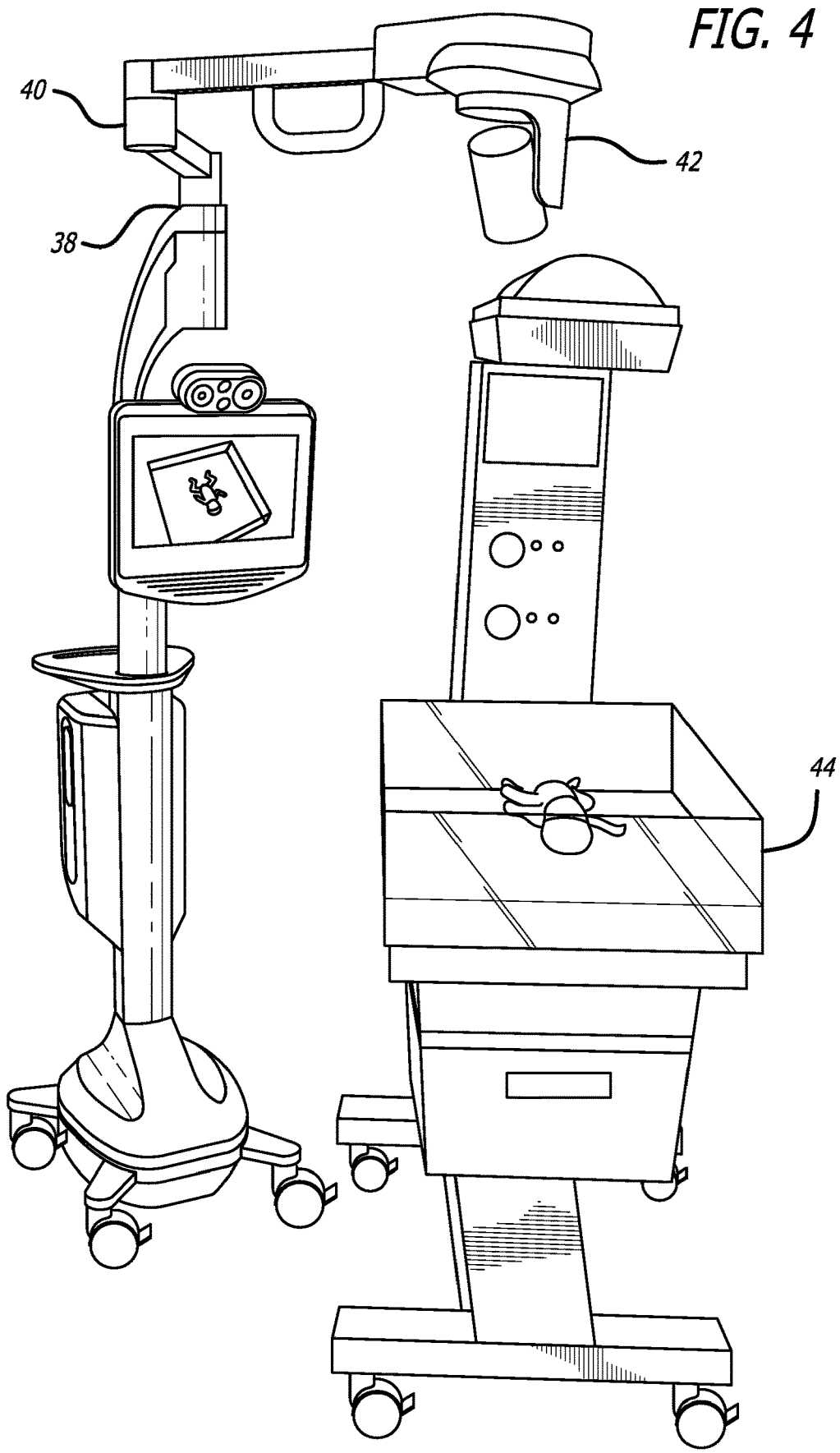
FIG. 4 illustrates an example of a telemedicine cart with an overhead boom camera installed in accordance with the disclosure.

The neck 16 extends up from the trunk 14 along a track (not shown) that runs vertically up the trunk. The neck 16 may be moved up or down along the track to shrink or elongate the neck 16 and vary the height of the head 18. The track may employ friction elements, latches, springs, and/or counter weights (not shown) to achieve smooth movement of the neck 16 along the track and ensure that the neck 16 and head 18 remain at the desired height when not being raised or lowered. The variable length of the neck 16 may allow the height of the head 18 to be varied from approximately four feet above the floor to six feet above the floor. The top of the neck 16 may include a mount point 38 adapted to receive one end of an articulating boom 40 that supports an additional, overhead pan-tilt-zoom (PTZ) camera 42, as shown in FIG. 4. This configuration is beneficial in, e.g., a neonatal intensive care environment in which local care providers will often surround an infant bed 44 and the overhead camera 42 is crucial for the remote care provider to view the infant. This configuration is also beneficial in any environment in which there is a sterile field that precludes moving the cart 10 within a certain distance of the patient without requiring subsequent sterilization, as is the case for many surgical procedures.

Figure 5A:
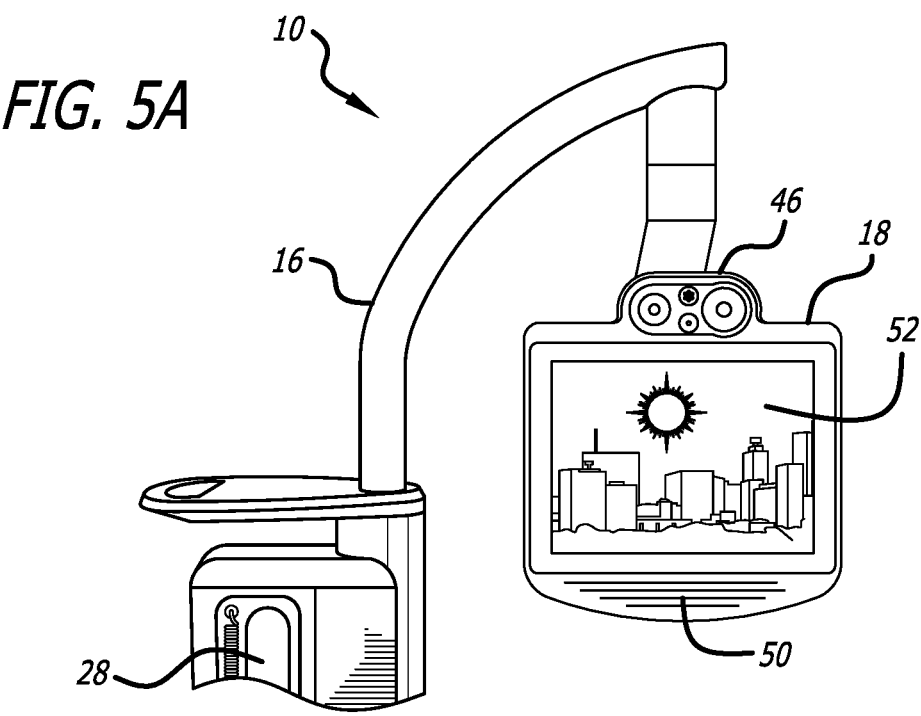
FIGS. 5A-B illustrate detailed views of the head of a telemedicine cart in accordance with the disclosure.
Figure 5B:
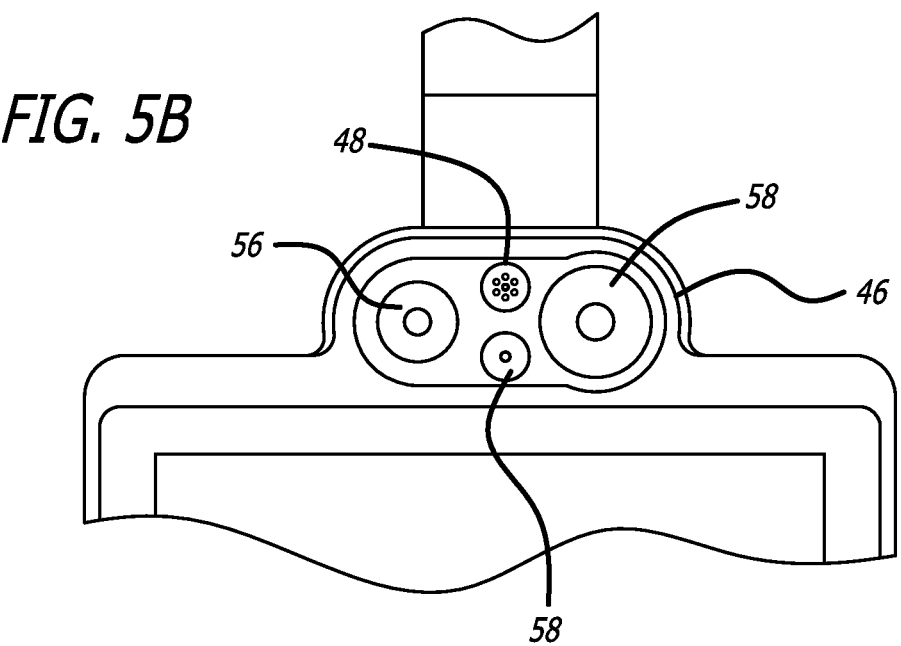

FIGS. 5A-B show an example of the head 18 of a cart in accordance with the disclosure. The head 18 includes a camera system 46, one or more microphones 48, one or more speakers 50, and a touchscreen display 52 all coupled to a controller (not shown), which may be located in the head, the base, or any other suitable location in the cart. The camera system 46 may include a first optical camera 54 having a wide field of view or viewing angle and a second optical camera 56 having a narrow field of view with a higher zoom factor than the first optical camera 54. The controller may stream video from both optical cameras 54, 56 over the network to the remote device for display simultaneously, or the controller may switch the video stream being sent to the remote device between the first optical camera 54 and the second optical camera 56 depending on the zoom factor or field of view requested by the user of the remote device. Further details of a multi-camera teleconferencing system are discussed in U.S. Pat. No. 9,198,728, filed Sep. 30, 2005, entitled "Multi-Camera Mobile Teleconferencing Platform", the contents of which are hereby incorporated by reference.

The camera system may also include a thermal camera 58. An example of a suitable thermal camera is the BOSON 320 Camera Core manufactured by FLIR. The thermal camera may aid a physician or care provider in diagnosing a variety of conditions that may be invisible to the eye or optical cameras 54, 56 but result in irregular or otherwise unusual heat patterns on the patient's body. For example, irregular heat patterns such as "hot spots" on the patient's body may be indicative of localized trauma, infection, or irritation. Other patterns such as asymmetric blood flow in the limbs or the face may be indicative of ischemic stroke or other conditions that result in irregularities in the patient's blood flow. In addition to spatial anomalies in the patient's body heat, the thermal camera 58 may allow a care provider to detect temporal irregularities in the patient's temperature by analyzing temperature trends in images from the thermal camera 58 taken over time. The system may also be configured to use computer vision techniques to analyze the images captured by the thermal camera 58 and automatically detect spatial and temporal temperature irregularities discussed above. Further details of the use of thermal imaging devices in medical and telemedicine applications can be found in U.S. patent application Ser. No. 13/111,208, filed May 19, 2011, entitled "Mobile Videoconferencing Robot System with Autonomy and Image Analysis", and U.S. application Ser. No. 14/091,292, filed Feb. 13, 2014, entitled "Enhanced Diagnostics for a Telepresence Robot", the contents of which are hereby incorporated by reference.

In addition, a user interface for the thermal camera 58 such as that discussed in U.S. Appl. No. 62/536,907, the contents of which are incorporated by reference, may be available either on the touchscreen display as well as at a remote device logged into the cart. This interface makes available certain features such as temperature and color thresholding and measuring a point-to-point temperature differential on the patient's body using cursors positioned by the user on the thermal image displayed in the interface.

Although their viewing angles and zoom factors may be different, the various cameras 54, 56, 58 of the camera system in the head 18 of the cart are closely positioned and similarly oriented so as to allow switching between their respective streams while maintaining a similar perspective of the environment. For example, each of the cameras may face the same direction and be positioned less than three inches apart.

Figure 6:
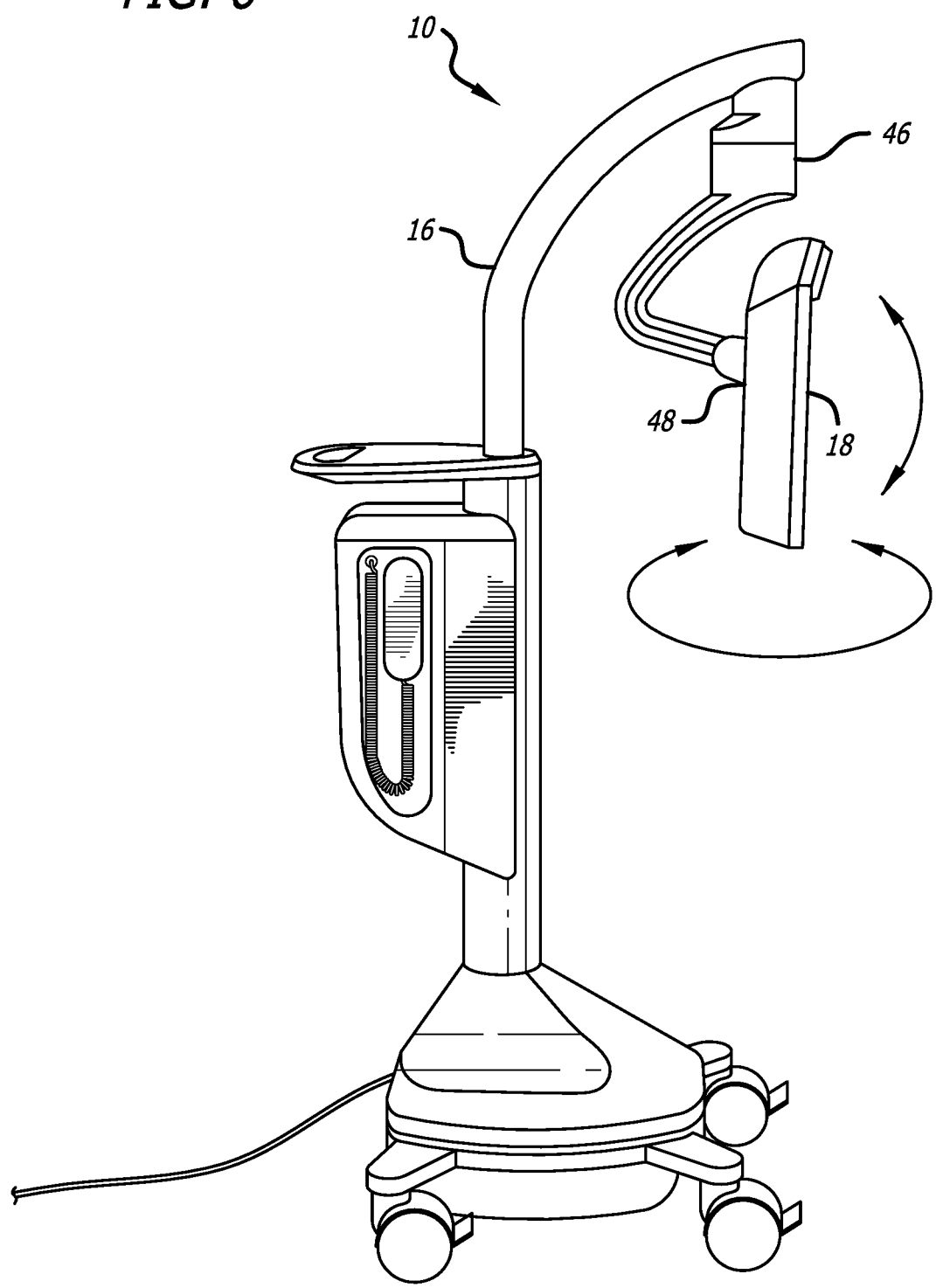
FIG. 6 illustrates another view of a telemedicine cart in accordance with the disclosure.

As shown in FIG. 6, the head 18 may be coupled to the neck 16 via a pan joint 46 and a tilt joint 48 that allow the head 18 to be panned and/or tilted relative to the neck 16. The joints 46, 48 may include motorized actuators that allow the pan and or tilt angles of the head 18 to be controlled remotely or via a control interface on the cart 10. The panning and tilting head 18 allows the remote user to reorient the camera system 46 to look around the environment surrounding the cart 10. The touchscreen display 52 may pan and tilt with the camera system 46 and always face the same general direction in which the camera system 46 faces. This creates the impression that the remote user is in the room and looking around the room in much the same way as a person actually in the room would. This provides an enhanced sense of the remote user's presence to people in the vicinity of the cart 10. The pan and tilt actuators between the neck 16 and the head 18 are also designed so as to allow the pan and tilt angle of the head 18 to be manually adjusted a user in the vicinity of the cart 10 by tilting or rotating the head 18 by hand.

Figure 7A:
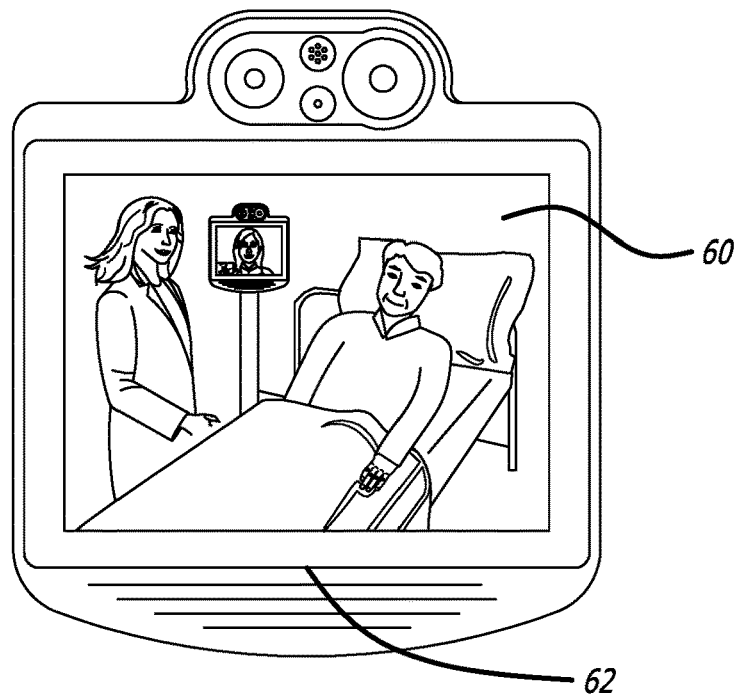
FIGS. 7A-D illustrate various screens of a user interface of a telemedicine cart in accordance with the disclosure.

FIG. 7A illustrates an example of a screen saver 60 that may be displayed as part of a user interface 62 on the touchscreen display 52 of the cart 10 when the system is idle. Touching the touchscreen 52 or otherwise interacting with the cart may cause the user interface 62 to transition the touchscreen display 52 from the screen saver 60 depicted in FIG. 7A to the menu 64 shown in FIG. 7B.

Figure 7B:
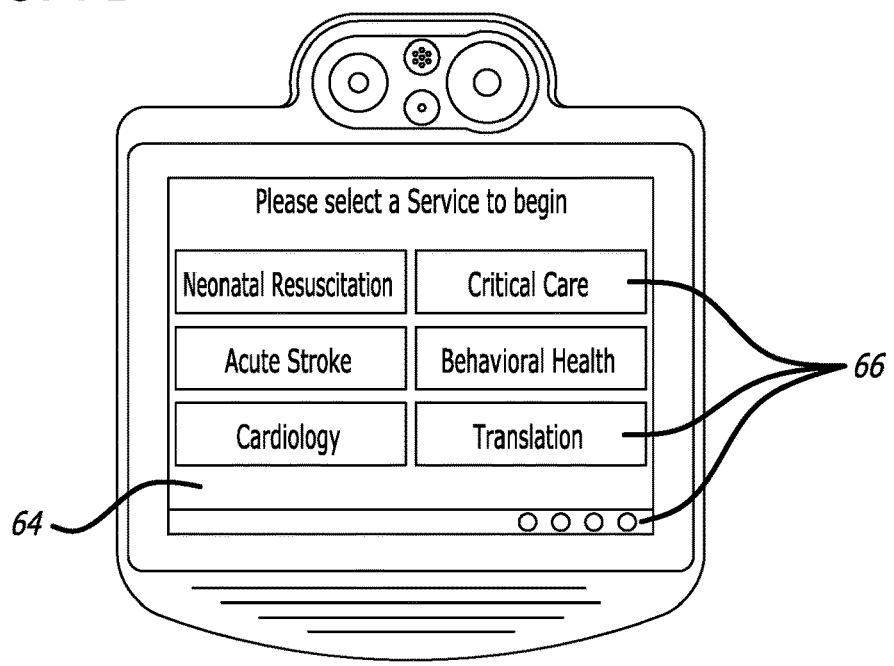

The menu illustrated in FIG. 7B may include a number of selectable options 66 including requesting a consultation with a remote physician or care provider. The menu 64 may display one or more different types of consultations, which may result in the request for consultation being sent to a specific care provider. Alternatively, any request for consult may simply sent to a general care coordination center with the requested type of consultation included in the request. Personnel at the care coordination center may then forward the request to the appropriate care provider. The various consultation types illustrated in FIG. 7B include neonatal resuscitation, critical care, acute stroke, behavioral health, and cardiologist. Those skilled in the art will recognize that many other types of consultations may be available for request.

Another selectable option 66 from the menu screen shown in 6B is "translation." When the user selects this option, the system may transmit a request for consult to a multi-lingual translator who can then log into the cart from their remote device and translate among parties who do not speak a common language. Upon selecting the translation option, the system may present another menu of specific language translation options (e.g., "Spanish", "French", etc.) that can be chosen to identify an appropriate translator. Alternatively, selecting the language translation option may send a request for a translator to personnel who may then locate an appropriate translator. The language translation service mode may include an option to mute video from any camera on the cart for privacy reasons.

The menu in FIG. 7B may also include a "friends and family" option that allows a user in proximity of the device to request a consultation with a member of the patient's family or friend group. When this option is selected, the touchscreen display may prompt the user for a telephone number, email address, or other communication address. The user may enter the requested information using alphanumeric keys displayed on the touchscreen, voice recognition, external keyboard, or other means. Once the requested information has been supplied, the controller may then transmit a message, e.g., a text message or email, to the provided address. The message may include a universal resource locator or other link that can be selected to launch a specific application on the recipients device that can connect to and establish a communication session with the cart via the internet. Alternatively, the link may simply direct a web browser on the recipients device to a web portal that allows the remote user's device to connect to and establish a communication session with the cart.

Figure 7C:
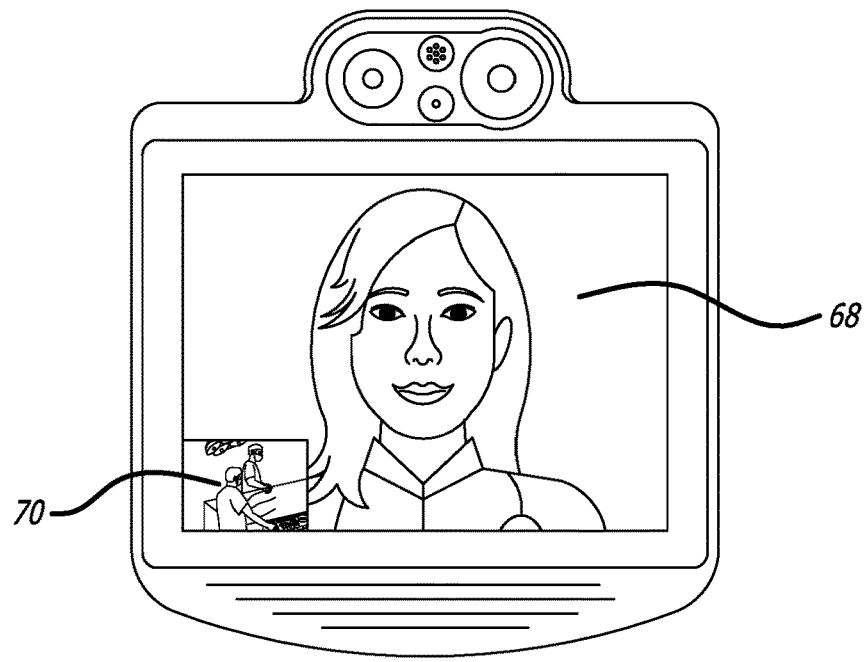

Once connected, or "in session," the cart may display video received from a camera of the remote user's device on the touchscreen display. In many cases, this video 68 will include the face of the remote user, as illustrated in FIG. 7C. In addition, video from the cart's camera system (or overhead camera) will be streamed to and displayed on a display of the remote user's device. This video may also be displayed on the touchscreen display of the cart in a picture-in-picture window 72. The cart microphone and speaker will be coupled to the speaker and microphone of the remote user's device so that people in the vicinity of the cart and the remote user(s) can hear each other.

By interacting the with user interface of the application on the remote device, the remote user can control the pan, tilt, and zoom of the camera system to look around the cart's environment. The remote user can also select to display video from any combination of the optical camera(s), the thermal camera, and the overhead camera. The user interface on the remote device may include a multi-view function that allows the user to simultaneously stream and view video from any two or more of the cameras coupled to the cart, including any imaging devices that may be connected to the cart's expansion bay, such as an otoscope or sonogram device. By way of example, the user may train the camera system to view the patients leg with the optical camera and simultaneously display video from the thermal camera to assist in identifying an irregular heat pattern on the patient's leg. Further details of an exemplary user interface for a remote device in telemedicine system can be found in U.S. application Ser. No. 10/962,829, filed Oct. 11, 2004, entitled "Graphical interface for a remote presence system", U.S. Pat. No. 9,361,021, filed Nov. 21, 2014, entitled "Graphical User Interfaces Including Touchpad Driving for Telemedicine Devices", and U.S. Pat. No. 9,098,611, filed Mar. 14, 2013, entitled "Enhanced Video Interaction for a User Interface of a Telepresence Network", the contents of which are hereby incorporated by reference.

Figure 7D:
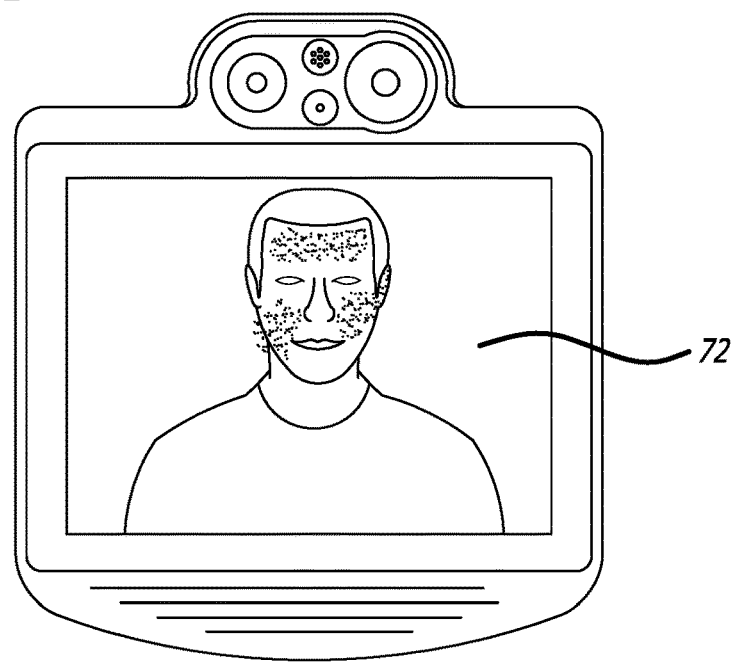

Another selectable option 66 available from the menu screen in FIG. 7B may be to display video from any imaging devices connected to the cart, including the optical camera(s), thermal camera, overhead camera, or any imaging devices connected to the expansion bay. For example, FIG. 7D illustrates an example of the touchscreen interface displaying a thermal video image 72 captured by the thermal camera on the cart. Even though the cart is not in session with a remote care provider, a local care provider may wish to view the patient's body using the thermal camera. In this case, the user may simply select, from the menu on the touchscreen display, to display the video from the thermal camera on the touchscreen display. The video from the thermal camera may then be displayed on the touchscreen and the user can adjust the height, pan, and/or tilt of the head to train the thermal camera on the desired part of the patient's body. The system may also allow the user to change the zoom factor of the displayed video using "pinch" or "spread" gestures on the touchscreen, or manipulating buttons or slider bars displayed on the touchscreen.

If the cart is configured with an the overhead boom camera, the touchscreen interface may also allow the user to display video from the overhead camera on the touchscreen interface and allow the user to adjust the pan, tilt, and zoom of the overhead camera. This is especially useful when the user is positioning the cart and adjusting the boom height in preparation for a consultation with a remote care provider who will utilize the overhead camera to view a sterile field or infant bed.

The menu displayed in FIG. 7B may also include an option for a local care provider to open or launch a clinical protocol, workflow, or otherwise open and edit a medical form or record using the touchscreen interface. For example, when a patient arrives for a telehealth consultation with a remote physician, a nurse or medical assistant may open a medical record for the patient using the touchscreen interface and begin documenting the encounter, including entering the patient's current vital signs into the record before the remote physician is notified that the patient is ready to begin the consultation. In another embodiment, if a patient arrives in an emergency department showing signs of a stroke, a nurse or doctor may launch a stroke consult form or workflow using the touchscreen interface and begin documenting the encounter and proceeding through the various steps prescribed in the medical facility's stroke protocol. Further details regarding editing patient records and documenting clinical encounters during a telemedicine encounter can be found in U.S. patent application Ser. No. 10/936,041, filed Sep. 7, 2004, entitled "Tele-presence system that allows for remote monitoring/observation and review of a patient and their medical records", U.S. Pat. No. 8,179,418, filed Apr. 14, 2008, entitled "A Robotic Based Health Care System", U.S. Pat. No. 8,849,680, filed Jan. 29, 2009, entitled "Documentation Through A Remote Presence Robot", and U.S. application Ser. No. 15/965,623, filed Apr. 27, 2018, entitled "Telehealth Cart that Supports a Removable Tablet with Seamless Audio/Video Switching", the contents of which are hereby incorporated by reference.

Figure 8:
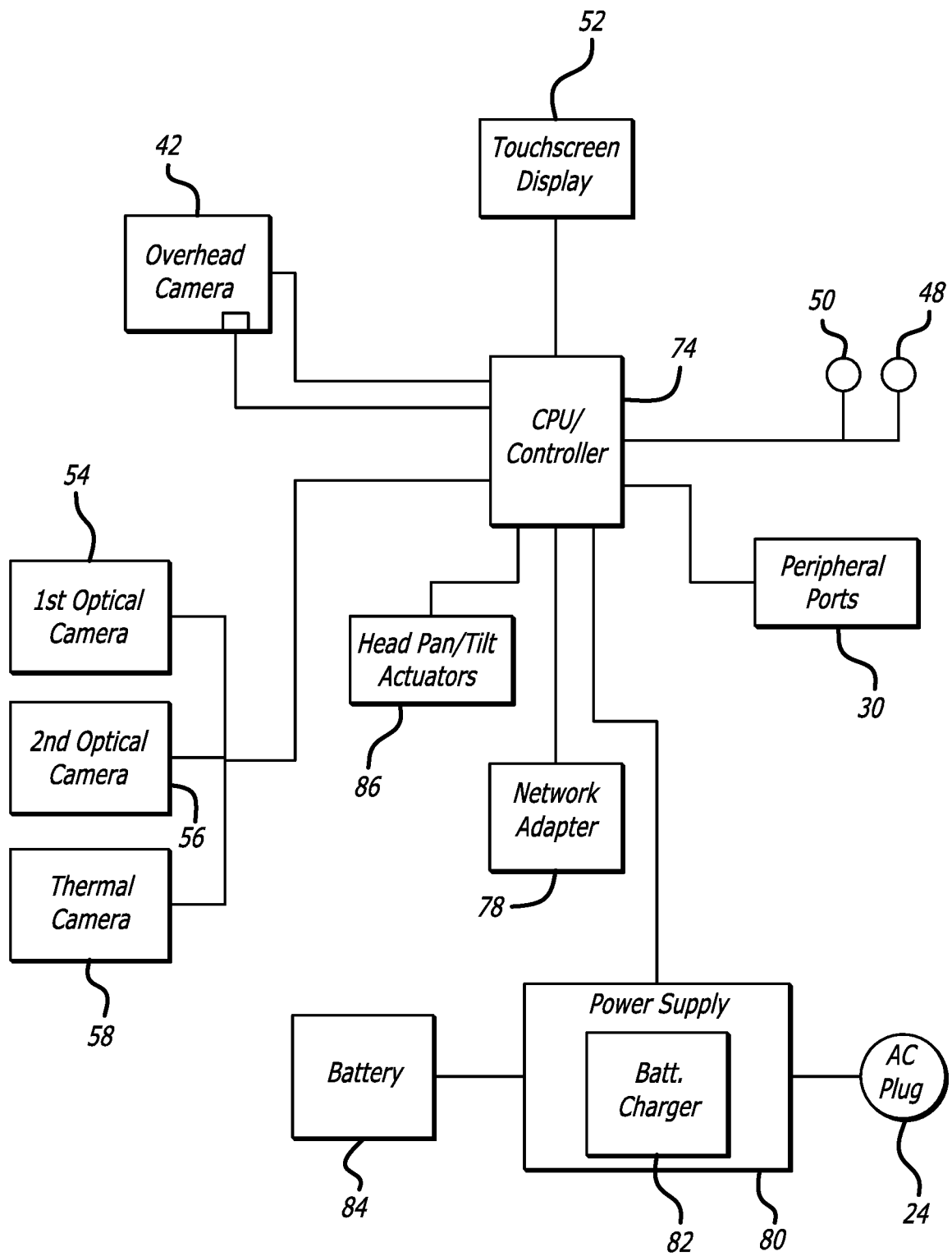
FIG. 8 is a block diagram of electronic components of a telemedicine cart in accordance with the disclosure.

FIG. 8 illustrates a block diagram of the various electrical components of a telemedicine cart in accordance with the disclosure. The cart includes a CPU or controller that may take the form of a computer running Microsoft Windows, LINUX, UNIX, MAC OS, or other similar operating system. The cart may include first and second optical cameras 54, 56 as well as a thermal camera 58 and an overhead camera 42. The overhead camera may be a PTZ camera and have a separate control interface 76, such as an RS-232 interface, that provides enhanced control of the actuators that control the pan, tilt, and zoom of the overhead camera 42. The cart may also include a touchscreen display 52 coupled to the controller 74 that can display images, including video and the user interface described above, as well as receive touch input from the user to provide to the controller. The cart may also include at least one speaker 50 and at least one microphone 48 coupled to the controller 74. The controller 74 is coupled to at least one network adapter 78 to allow the controller 74 to communicate with other devices over a network, such as the Internet. The one or more network adapters 78 may include wired network adapters (such as Ethernet) and wireless network adapters such as WIFI and Bluetooth. The cart may also include a peripheral port expansion bay 30 coupled to the controller 74. The peripheral ports may include HDMI, Ethernet, USB, and other interfaces for connecting to external medical devices, imaging devices, audio devices, input devices, and the like. The cart also includes an AC plug 24 coupled to a power supply 80 that powers the various electrical components of the cart. The power supply 80 may include a battery charger 82 coupled to a battery 84 to power the cart when the AC plug 24 is not plugged into an AC power source. Some components, such as the optical and thermal cameras, the touchscreen display, the microphone, and the speaker may be mounted together in the head of the cart which may have pan and tilt control provided by head pan/tilt actuators 86, which are coupled to and controlled by the controller 74.

Additionally, as will be appreciated by one of ordinary skill in the art, principles of the present disclosure may be reflected in a computer program product on a computer-readable storage medium having computer-readable program code embodied in the storage medium, the computer-readable program code executable by a processor. Any tangible, non-transitory computer-readable storage medium may be utilized, including magnetic storage devices (hard disks, floppy disks, and the like), optical storage devices (CD-ROMs, DVDs, Blu-Ray discs, and the like), flash memory, and/or the like. These computer program instructions may be loaded onto a general purpose computer, special purpose computer, or other programmable data processing apparatus to produce a machine, such that the instructions that execute on the computer or other programmable data processing apparatus create means for implementing the functions specified. These computer program instructions may also be stored in a computer-readable memory that can direct a computer or other programmable data processing apparatus to function in a particular manner, such that the instructions stored in the computer-readable memory produce an article of manufacture, including implementing means that implement the function specified. The computer program instructions may also be loaded onto a computer or other programmable data processing apparatus to cause a series of operational steps to be performed on the computer or other programmable apparatus to produce a computer-implemented process, such that the instructions that execute on the computer or other programmable apparatus provide steps for implementing the functions specified.

The foregoing specification has been described with reference to various embodiments. However, one of ordinary skill in the art will appreciate that various modifications and changes can be made without departing from the scope of the present disclosure. Accordingly, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, a required, or an essential feature or element. As used herein, the terms "comprises," "comprising," and any other variation thereof, are intended to cover a non-exclusive inclusion, such that a process, a method, an article, or an apparatus that comprises a list of elements does not include only those elements but may include other elements not expressly listed or inherent to such process, method, system, article, or apparatus. Also, as used herein, the terms "coupled," "coupling," and any other variation thereof are intended to cover a physical connection, an electrical connection, a magnetic connection, an optical connection, a communicative connection, a functional connection, and/or any other connection.

While the principles of this disclosure have been shown in various embodiments, many modifications of structure, arrangements, proportions, elements, materials, and components, which are particularly adapted for a specific environment and operating requirements, may be used without departing from the principles and scope of this disclosure. These and other changes or modifications are intended to be included within the scope of the present disclosure.

What is claimed is:

1. A telemedicine system comprising:
a cart that supports a controller coupled to a camera system, a touchscreen display, a microphone, a speaker, and a network, the controller is configured to display a user interface on the touchscreen display in response to a user input received via the touchscreen display, the user interface including at least a first selectable option that causes video captured by the camera system to be displayed on the touchscreen display when the system is not in session and a second option to transmit a request for consultation via the network,
wherein the controller is configured to establish a communication session with a remote device coupled to the controller via the network, the remote device including a camera, a display, a microphone, and a speaker and, during the communication session, the controller causes the touchscreen display to display video captured by the camera of the remote device.

2. The system of claim 1, wherein the camera system includes a thermal camera.

3. The system of claim 2, wherein the camera system includes a first optical camera with a first field of view.

4. The system of claim 3, wherein the camera system includes a second optical camera with a second field of view.

5. The system of claim 4, wherein the cart further comprises an articulating boom that supports a third optical camera coupled to the controller, the third optical camera having a third field of view.

6. The system of claim 5, wherein the third optical camera is a pan-tilt-zoom camera.

7. The system of claim 6, wherein the controller changes at least one of the pan, tilt, and zoom of the third optical camera in response to a user input provided via the touchscreen display.

8. The system of claim 6, wherein the controller changes at least one of the pan, tilt, and zoom of the third optical camera in response to a user input received from the remote station.

9. The system of claim 1, wherein the camera system and the touchscreen display can be panned and tilted relative to the cart.

10. The system of claim 9, wherein the camera system and the touchscreen display are mechanically coupled such that they face in substantially the same direction and move together.

11. The system of claim 9, wherein the cart includes actuators configured to pan and tilt the camera system and the touchscreen display in response to commands received from the remote station.

12. The system of claim 11, wherein the actuators are configured to be manually repositioned by a person in the vicinity of the cart.

13. The system of claim 1, wherein the user interface displays a plurality of selectable consultation types that can be selected to request a consultation.

14. The system of claim 13, wherein selecting a first consultation type cause a consultation request to be transmitted to a first care provider and selecting a second consultation type causes a consultation request to be transmitted to a second care provider.

15. The system of claim 1, wherein the user interface includes a selectable option that causes the controller to display a medical form that can be completed via the touchscreen interface.

16. The system of claim 1, wherein the controller causes the user interface to display a prompt for a telephone number and subsequently transmits the consultation request to a telephone number provided by the user via the touchscreen interface in response to the prompt.

17. The system of claim 1, wherein the consultation request is transmitted via a Short Message Service protocol and includes a uniform resource locator.

18. The system of claim 17, wherein the recipient of the consultation request can select the uniform resource locator to activate an application that establishes the communication session with the controller.

19. The system of claim 1, wherein the user interface includes a selectable option for a language translation service.

20. The system of claim 1, wherein the cart includes a removable peripheral bay that includes a plurality of communication ports coupled to the controller.

* * * * *